United States Patent [19]

Fellers et al.

[11] Patent Number: 5,622,995*

[45] Date of Patent: Apr. 22, 1997

[54] METHODS FOR CONTROL AND MITIGATION OF MOLLUSCS

[75] Inventors: Billy D. Fellers, Glen Rose, Tex.; Arthur J. Freedman, Lebanon, N.J.; Thomas M. Laronge, Vancouver, Wash.

[73] Assignee: Electric Power Research Institute, Inc., Palo Alto, Calif.

[21] Appl. No.: 290,450

[22] Filed: Aug. 15, 1994

Related U.S. Application Data

[63] Continuation of Ser. No. 578,812, Sep. 6, 1990, abandoned.

[51] Int. Cl.⁶ .......................... A01N 33/04; A01N 33/08; C02F 1/50

[52] U.S. Cl. .......................... 514/667; 514/663; 514/664; 514/668; 514/670; 514/671; 514/673; 514/674; 210/749; 210/764

[58] Field of Search .................................. 514/663, 664, 514/667, 668, 670, 671, 673, 674, 918; 210/749, 764; 424/78.09

[56] References Cited

U.S. PATENT DOCUMENTS

| | | | |
|---|---|---|---|
| 4,269,820 | 5/1981 | Davies et al. | 424/10 |
| 4,462,914 | 7/1984 | Smith et al. | 210/755 |
| 4,643,835 | 2/1987 | Koiplin-Gall et al. | 210/754 |
| 4,789,489 | 12/1988 | Hollis et al. | 210/755 |
| 4,970,239 | 11/1990 | Whitekettle et al. | 514/665 |
| 5,141,754 | 8/1992 | Ekis, Jr. et al. | 424/661 |
| 5,154,857 | 10/1992 | Durrieu et al. | 252/338 |
| 5,503,836 | 4/1996 | Fellers et al. | 424/405 |

FOREIGN PATENT DOCUMENTS

| | | |
|---|---|---|
| 457439A1 | 11/1991 | European Pat. Off. . |
| 52-10418 | 1/1977 | Japan . |
| 52-79024 | 7/1977 | Japan . |
| 54-110323 | 8/1979 | Japan . |
| 54-110322 | 8/1979 | Japan . |
| 55-143902 | 11/1980 | Japan . |
| 56-25102 | 3/1981 | Japan . |
| 57-21301 | 2/1982 | Japan . |

OTHER PUBLICATIONS

Soviet Patents Abstracts, issued Jan. 10, 1990, AN:89-346323/47; abstracting SU1456373 (Feb. 7, 1989).
Database WPI, Derwent Publications Ltd, London (GB), AN: 77-58386Y/33; abstracting JP 52-79024 (Jul. 2, 1977).
Database WPI, Derwent Publications Ltd, London (GB); AN: 77-17248Y/10; abstracting JP 52-10418 (Jan. 26, 1977).
Patent Abstracts of Japan, vol. 5 (75), issued May 19, 1981; abstracting JP 56-25102 (Mar. 10, 1981).
Central Patents Index, Basic Abstracts Journal, Derwent Publications Ltd., London (GB), AN: 12540D/08, issued Apr. 15, 1981; abstracting JP55-160701 (Dec. 13, 1980).
Central Patents Index, Basic Abstracts Journal, Derwent Publications Ltd., London (GB), AN: 1007D/02, issued Mar. 4, 1981; abstracting JP 55-143902 (Nov. 10, 1980).
Central Patents Index, Basic Abstracts Journal, Derwent Publications Ltd., London (GB), AN: 20410E/11, issued May 12, 1982; abstracting JP 57-21301 (Feb. 4, 1982).
Central Patents Index, Basic Abstracts Journal, Derwent Publications Ltd., London (GB), AN: 71371E/34, issued Oct. 20, 1982; abstracting JP 57-116004 (Jul. 19, 1982).
Database WPI, Derwent Publications Ltd, London (GB), AN 78-62755A/35; abstracting JP 53-86029 (Jul. 29, 1978).
Supplementary European Search Report; Appl. No. EP 91 91 8479 (Feb. 1994).
Cameron (I) et al., "Minimizing the formation . . . " Am. Water Works Assoc. J., vol. 81 (10), 1989 (Oct.), pp. 53–62.
Cameron (II) et al., "Effect of Temperature and pH on the Toxicity . . . " Am. Water Works Assoc. J., vol. 81 (10), Oct. 1989, pp. 62–71.
Chemical Abstracts 71: 12044w, 1969.
Jenner, H., "Control of Mussel Fouling in the Netherlands: Experimental and Existing Methods", Symposium on Condenser Macrofouling Control Technologies, Electric Power & Research Company, Palo Alto, CA, 1983.
McMahon, R. "Primer on the Asian Clam *Corbincula fulminea*", Jun. 23, 1988 University of Texas at Arlington, Texas.
Kajdasz, R. "Biocidal Efficacy with Respect to Sessile and Planktonic Organisms", Dearborn Chemical Company, Nashville, Tennessee, 1984.
McMahon, R.—"Ecology of an Invasive Pest Bivalve, Corbidula," W.D. Russell–Hunter (ed.), *The Mollusca*, vol. 6, Ecology, pp. 505–561, 1983, Academic Press, New York.
Jenner, H., "Chlorine Minimization in Macrofouling . . . Control in the Netherlands", Ann Arbor Science Publishers, vol. 5, pp. 1425–1434, 1984.
Jenner, H. "A Microcosm Monitoring Mussel Fouling", Symposium on Condenser Macrofouling Control Technologies, Electric Power and Research Company, Palo Alto, CA 1983.
McMahon, R., "Effects of Two Molluscicides on the Freshwater Macrofouling and Bivalves *Corbicula fluminea* and *Dresissena polymorpha*", Symposium on Condenser Macrofouling Control Technologies, Electric Power and Research Company Palo Alto, CA, 1983.
McMahon, R., "Mollusca: Bivalvia," Academic Press Volume Ecology and Systematics of North American Freshwater Invertebrates, Chapter 11, Feb. 16, 1990, The University of Texas at Arlington, Texas.

*Primary Examiner*—John Pak
*Attorney, Agent, or Firm*—Fish & Richardson P.C.

[57] ABSTRACT

A method is provided for controlling the proliferation of molluscs in target habitat by applying to the habitat a compound or mixture of compounds which are amines, ethoxylated amines, quaternary amines, ethoxylated quaternary amines and cyclic amines.

6 Claims, No Drawings

METHODS FOR CONTROL AND MITIGATION OF MOLLUSCS

This is a continuation of application Ser. No. 07/578,812 filed Sep. 6, 1990 now abandoned.

BACKGROUND OF THE INVENTION

The present invention is directed to methods of control and mitigation of molluscs and in particular, the control of molluscs for macrofouling control within industrial cooling water systems and within municipal water supply systems. The bi-valve molluscs *Dreissena polymorpha* (Zebra mussel) and *Corbicula fluminea* (Asian clam) are macrofouling species capable of settling in the service water systems (SWS) of electric power stations, water treatment stations, and other industrial systems which use fresh water from lakes and streams for heat exchange purposes. These molluscs can grow in sizes to reduce or block flow in small diameter piping or heat exchangers. For *C. fluminea*, the problem primarily stems from the small juvenile molluscs which become suspended in intake waters and settle in low flow areas (such as the bottom of large diameter piping, pipe bends, reservoirs, etc.). Once settled in these flow areas, the juveniles grow rapidly to sizes that will block the small diameter tubings. After growing to sizes capable of fouling the system components, the *C. fluminea* may crawl or be carried by water currents from the low flow areas into high flow piping where they are transported to other areas where their shells become lodged as constrictions in the tubing, thereby restricting or blocking flow.

The mode of action of *D. polymorpha* is somewhat different. The small larvae are carried into the intake on water currents and settle in the low flow areas very similar to those described for *C. fluminea*. However, unlike *C. fluminea* which burrow into the sediment accumulated in the low flow areas, *D. polymorpha* adults produce proteinaceous byssal threads from abyssal gland at the base of their foot to attach to hard surfaces. Since the juvenile *D. polymorpha* preferentially settle on open, hard surfaces, but also attach on the shells of attached adults, mats of mussels many shells thick develop in low flow areas. Moreover, dead mussel shells and mats of mussel shells may break loose from the walls of the low flow areas and are carried into macrofouling sensitive components such as heat exchangers. Since the adults attach by byssal threads to hard surfaces (including boat hulls) and the larvae remain for extended periods in the plankton, *D. polymorpha* have extensive capacity for dispersal by both natural and human mediated mechanisms and it, along with *C. fluminea*, will become a major macrofouler of power station water systems and other raw water systems.

The conventional control for both *C. fluminea* and *D. polymorpha* in water systems primarily involves constant application of chlorine in free residual level of about 0.3 to 0.5 ppm. Even at these levels, continuous chlorination may not exclude mollusc and the presence of chlorine enhances corrosion rates. Additionally, chlorination is under close regulatory scrutiny in many areas. More recently, a number of nonoxidizing toxicants, typically known as biocides, have been used as molluscicides. The prior art is composed primarily of many different types of toxic and persistent organic compounds, for example, thiocarbanates are common. Some aromatic (i.e. benzene ring) quaternary amine and cyanide molluscicides are known, but these compounds are also toxic to non-target aquatic species at or below their effective concentrations for mollusc control. Also, these compounds are often resistant to biodegradation and may not be well suited for application to potable water supplies. Further, some of the prior art, i.e. aromatic compounds, may persist in the environment and not be readily biodegradable. Therefore, there is a need to develop effective, environmentally acceptable, non-oxidizing molluscicides for control of bi-valve macrofouling.

Moreover, it would be desirable to provide such molluscicides which can be used at concentrations which can, on the one hand, control the proliferation of the molluscs, but on the other hand, be effective for that use at concentrations which have a substantially lower impact for non-target species to improve their environmental acceptability and to further be suitable for potable applications. Many conventional oxidizing and non-oxidizing biocides which are utilized are so active by environmental protection standards, that they often require detoxification treatment to support their use. A molluscicide which does not require detoxification treatment would therefore be desired.

It is therefore an object of the present invention to provide a method for controlling proliferation of molluscs by applying a class of chemicals to this habitat which have been found to be effective to control their proliferation, particularly of *D. polymorpha* and *C. fluminea*, at effective amounts which are below toxicity levels, which are biodegradable and which are more acceptable for potable water systems.

It is a further object of the present invention to provide a method for controlling proliferation of molluscs utilizing chemicals which, in addition to their molluscicide activity, have a chemical effect on byssal attachment of molluscs as an additional macrofouling control mechanism.

These and other objects will be apparent from the following description and from the practice of the invention.

SUMMARY OF THE INVENTION

The present invention provides a method for controlling and mitigating macrofouling by molluscs, particularly *D. polymorpha* and *C. fluminea* which are present in the waters in the system in which macrofouling inhibition is required, treating these waters with a mollusc proliferation-controlling amount of composition comprising one, or a mixture of compounds, selected from the group consisting essentially of amines, ethoxylated amines, non-aromatic quaternary amines, ethoxylated non-aromatic quaternary amines and cyclic amines. Preferred embodiments of use of such compounds are disclosed. The dosage of the composition required to effectively control the proliferation of the molluscs may be as low as about 1.0 mg/liter and up to as much as about 20 mg/liter depending on the selected treatment regime. Effective treatment regimes include, but are not limited to continuous low level applications, discontinuous or intermittent applications of low to medium concentrations, and higher level slug type treatments. These variations may be practiced under static or flowing conditions. The present invention provides control through mortality of the molluscs, by control of their attachment to, and by their detachment from substrates.

DESCRIPTION OF THE PREFERRED EMBODIMENTS

Particularly preferred amines include aliphatic amines, fatty amines, their amine salts; and non-aromatic quaternary amines. Preferred aliphatic amines may have alkyl or aryl groups ranging from about $C_2$ to $C_{22}$ which may include ethoxylated or propoxylated derivatives thereof. Cyclic amines, may be hydroxylated or ethoxylated imidazolines or other cyclic amines.

Exemplary non-aromatic quaternary amines and ethoxylated non-aromatic quaternary amines which are effective at application rates which are less toxic to non-target aquatic species than prior art aromatic quaternary amine molluscicides, include polyethoxylated fatty amines. A particularly preferred class of quaternary amines include the chemicals sold under the trademark of Ethoquad by Akzo Chemicals Inc. A particularly preferred quaternary amine is Ethoquad C/12-75 which is a cocoalkylmethyl ethoxylate of a quaternary ammonium salt. Further exemplary quaternary amines include methylated coco derivatives. A particularly preferred class of quaternary amines include the chemicals sold under the trademark of Arquad by Akzo Chemicals Inc. A particularly preferred quaternary amine is Arquad 2C-75 which is a dicocodimethyl-ammonium chloride.

Exemplary fatty amines include aliphatic amines and ethoxylated aliphatic amines. A particularly preferred class of fatty amines includes chemicals sold under the trademark of Duomeen, Ethomeen and Ethoduomeen by Akzo Chemicals Inc. Particularly preferred fatty amines include Duomeen C which is an N-Alkyl propane diamine, Ethomeen 0/12 which is an ethoxylated tertiary oleylamine and Ethoduomeen T/13 which is an ethoxylated N-tallow fatty diamine.

Exemplary cyclic amines include imidazolines and amines of coco and oleic hydrophobes. Particularly preferred classes of imidazolines includes chemicals sold under the trademark of Alkazine by Alkaril Chemicals and the trademark of Monazoline by Mona Industries Inc. Particularly preferred imidazolines include Alkazine C which is a Coco hydroxyethyl imidazoline, by Alkaril, and Monazoline O which is a substituted oleic acid imidazoline, a cyclic tertiary amine, by Mona.

The present invention provides a method for controlling the proliferation of mollusc in a target habitat comprising the step of periodically or continuously applying to this habitat a composition comprising one, or a mixture of two or more, of the above-identified compounds. The amine compounds according to the present invention, are characterized by their properties as salts, their aliphatic hydrophobes and ethoxylated and propoxylated derivatives thereof.

It is well known that cationic amine compounds may exhibit general toxicity or biocide properties, particularly aromatic quaternary amines and compounds containing thiocarbonates and cyanides, which are exemplary of the prior art. This general toxicity often exists at or below the use concentrations as molluscicides. Furthermore, many of these compounds give rise to biodegradation issues.

The compounds of the present invention are distinguishable from the prior art by the virtue of their aliphatic, straight chain, characteristic and the absence of benzyl groups, thiocarbonates, cyanides or other related toxicants. Therefore, this characteristic is preferred within the current invention to improve acceptability to potable applications improved biodegradability and because of their efficacy at concentrations lower than their general purpose biocide or general toxicity limits.

The exemplary compounds described herein are active as molluscicides. Aliphatic chain lengths in the range from $C_8$ to $C_{20}$ or higher, and mole percent ethoxylation, proxoxylation and mixed ethoxylation/propoxylation in the range from 1 to 40 or higher, should all be active. The compounds utilized in accordance with the invention, may also be used in formulations with other compounds, for other desired properties, e.g., solubility, substantivity to surfaces, foam level, etc.

It will be apparent to those skilled in the art that, based on the discoveries explained herein, formulated products can be used to enhance performance in specific applications, both using molluscicides alone and with oxidizing biocides or other toxicants. Further, the efficacy of molluscicides of the current invention may be enhanced by various types of dispersants which improves distribution, solubility and penetration of the chemical compounds. Synergism of toxic molecules with various types of dispersants, surfactants and wetting agents in water systems has been well established in the literature. Dispersants, surfactants and wetting agents reduce surface and interfacial tension, and thereby improve the ability of toxicants in water to penetrate biomass. They also improve wetting of both hard surfaces, e.g. mollusc shells and biological surfaces, e.g. gills, etc., thus increasing exposure of organisms to the toxic molecules. All of these effects may be expected to occur with mixtures of the molecules of this invention and common dispersants, surfactants and wetting agents. It is apparent therefore that the above-identified compounds may be administered alone or in combination with other known molluscicides and various types of dispersants or carrier compounds.

Static Testing

To illustrate the efficacy of the compounds utilized in accordance with the present invention, specimens of Zebra mussels (*D. polymorpha*) were obtained from various stations in the midwest United States and held in a 75 gallon tank, constantly aerated, refrigerated at about 50° F. until utilized in the tests. Also, Asian Clams (*C. fluminea*) were obtained from various water sources in the north central Texas area and were exposed to the same chemicals. The static tests were carried out at 68°–73° F. in a constant temperature laboratory in which the mussels were habituated for 7 days prior to any experimentation. The mussels were exposed to various concentrations of various agents within the scope of the present invention in 5 gallon plastic aquaria containing 4.5 gallons of an appropriate medium. Water in the test aquaria was constantly aerated and circulated. Media in the tanks were made by mixing appropriate concentrated stock solutions of the agents with dechlorinated tap water. Control tanks contained only the dechlorinated city water. Individual mussels of sizes ranging from recently settled juveniles, less than 1 centimeter long, to adults several years old, greater than 2.5 centimeters long, were tested. Samples of mussels (n=15 individuals per dish, 30 individuals in 2 dishes per tank, 210 mussels per experiment) were placed in 4×4×1 inch high glass dishes in the bottom of each 5 gallon test aquaria, initially containing only the dechlorinated city water. The shells of all mussels were etched with a permanent identifying mark and their shell length measured to the nearest 0.1 mm. Individuals were held in one of these dishes for 3 days prior to experimentation in the tanks to allow them to form byssal thread attachments. Another group of 15 individuals were placed in a second dish in each tank immediately prior to biocide exposure. This second group of mussels did not have time to form new byssal attachment threads before being exposed to the test agent. Thus, a group of 15 attached and 15 unattached mussels were placed in each of the 7 tanks (6 experimental, 1 control). Additionally 15 adult Asian clams were placed within each tank. Immediately after placement in the tanks, the appropriate amount of the chemical agent was added to achieve the desired test concentrations. Thereafter, the media in the tanks were replaced every 3 to 4 days to maintain chemical titre and to remove any waste products which could be deleterious to the mussels. The behavior of the individuals, i.e., the number with open valves, normally syphoning water over the gills and the number with the valves shut were determined during each evaluation. The number of mussels attached and detached from the byssus were determined for each group in the tank, by probing each individual gently with a blunt glass rod. Byssally attached individuals cannot be displaced by gentle probing with a glass rod while unattached individuals are readily displaced. The number of living and dead individuals were determined at each observation. Dead mussels and clams were identified by gently touching the syphons and exposed mantle tissues at the posterior end of each individual in each sample with a blunt tip of a glass rod. The response to such stimulation to a living individual is to immediately clamp the valve shut. If no response is elicited, a second, stronger stimulation with the glass rod is given. If no valve closure response is observed after the second stimulation, an individual was considered dead. Upon death, individuals were removed from the test aquaria.

Further testing was conducted using the same protocol but limiting the exposure to chemicals for 24 hours, followed by placement in clean untreated waters. These tests were designed to study latent mortality in support of discontinuous treatment regimes.

Additionally, a similar protocol was employed to elicit any synergy of non-oxidizing chemicals of this invention and chlorine, a strong oxidant. In general, this potential is evidenced by the stress symptoms as observed after exposure to the non-oxidizing compounds which increases susceptibility to more potent oxidizing compounds. These tests included a 24 hour exposure to the non-oxidizing molluscicide followed by either 2 or 4 hours of exposure to 2.0 mg/liter chlorine. The latent mortality of zebra mussels exposed only to the molluscicide and to both the molluscicide and chlorine, was determined separately. The lack of efficacy by chlorine, for short-term exposures, is so well documented in the open literature that duplicate tests were not justified.

The tests were conducted with successful results using those chemicals (A through G) listed in Table 1 which further discloses their physical properties.

TABLE 1

| Classification | | Sub Classification | Typical Tradename | Manufacturer |
|---|---|---|---|---|
| 1. | Quaternary Amine and Ethoxylated Quaternary Amines | A. ethoxylated | Ethoquad C/12–75 | AKZO |
|  |  | B. dialkyl quat | Arquad 2C-75 | AKZO |
| 2. | Amines and Ethoxylated Amines | C. ethoxylated diamine | Ethoduomeen T/13 | AKZO |
|  |  | D. ethoxylated tertiary amine | Ethomeen 0/12 | AKZO |
|  |  | E. diamine | Duomeen C | AKZO |
| 3. | Cyclic Amines and Imidazolines | F. hydroxyethyl imidazoline | Alkazine C | Alkaril |
|  |  | G. cyclic tertiary imidazoline | Monozoline 0 | Mona |

Efficacy Against Attached Adult *D. polymorpha*

Chemicals within all the group classifications demonstrated excellent efficacy against attached *D. polymorpha* as shown in Table 2. These chemicals could be ranked by their performance in the order C>E>F>A>B>G>D. In general, the diamines and ethoxylated diamines provided superior efficacy against attached *D. polymorpha* followed by the imidazoline, ethoxylated quaternary amines and quaternary amines. Both the cyclic tertiary amine and ethoxylated tertiary amine provided lower efficacy.

TABLE 2

Efficacy Against Attached *D. polymorpha*

| Chemical | Days of Observation | | | | | | | |
|---|---|---|---|---|---|---|---|---|
|  | 1 | 2 | 3 | 4 | 5 | 6 | 7 | 8 |

2A. Cumulative Mortality for Continuous Chemical Exposure

| Controls | 0 | 0 | 0 | 0 | 0 | 0 | 0 | 0 |
|---|---|---|---|---|---|---|---|---|
| $A_{25}$ | 0 | 0 | 0 | 0 | 0 | 0 | 0 | 0 |
| $A_1$ | 0 | 0 | 0 | 0 | 0 | 0 | 0 | 0 |
| $A_5$ | 0 | 0 | 7 | 67 | 93 | 100 | 100 | 100 |
| $A_{10}$ | 0 | 0 | 13 | 53 | 100 | 100 | 100 | 100 |
| $B_5$ | 0 | 0 | 0 | 67 | 93 | | | |
| $B_{10}$ | 0 | 0 | 13 | 100 | 100 | | | |
| $C_{.25}$ | 0 | 0 | 0 | 0 | 0 | | | |
| $C_1$ | 0 | 0 | 0 | 0 | 0 | 0 | 7 | 7 |
| $C_5$ | 13 | 20 | 67 | 100 | 100 | 100 | 100 | 100 |
| $C_{10}$ | 33 | 40 | 87 | 100 | 100 | 100 | 100 | 100 |
| $D_5$ | 0 | 0 | 0 | 0 | 0 | | | |
| $D_{10}$ | 0 | 0 | 7 | 40 | 60 | | | |
| $E_5$ | 0 | 0 | 60 | 100 | 100 | | | |
| $E_{10}$ | 0 | 13 | 73 | 100 | 100 | | | |
| $F_{10}$ | 0 | 0 | 53 | 93 | 100 | | | |
| $G_{10}$ | 0 | 0 | 27 | 60 | 80 | | | |

2B. Latent Mortality (Percent) After 24 Hours Chemical Exposure

| $A_5$ | 0 | 0 | 20 | 50 | 50 | 50 | | |
|---|---|---|---|---|---|---|---|---|
| $C_{10}$ | 0 | 13 | 33 | 60 | 67 | | | |

The subscript denotes concentration in mg/liter.

Efficacy Against Unattached Adult *D. polymorpha*

In all cases the tested chemicals demonstrated excellent and typically higher efficacy against unattached *D. polymorpha* as shown in Table 3, these chemicals could be ranked by their performance in the order C>E>A>F>B>G>D>. This performance ranking is comparable to that for efficacy against attached *D. polymorpha* including the performance by chemical group classifications.

TABLE 3

Efficacy Against Unattached *D. polymorpha*

| Chemical | Days of Observation | | | | | | | |
|---|---|---|---|---|---|---|---|---|
|  | 1 | 2 | 3 | 4 | 5 | 6 | 7 | 8 |

3A. Cumulative Mortality for Continuous Chemical Exposure

| Controls | 0 | 0 | 0 | 0 | 0 | 0 | 0 | 0 |
|---|---|---|---|---|---|---|---|---|
| $A_{25}$ | 0 | 0 | 0 | 0 | 0 | 0 | 0 | 0 |
| $A_1$ | 0 | 0 | 0 | 7 | 7 | 7 | 7 | 7 |
| $A_5$ | 0 | 33 | 40 | 93 | 100 | 100 | 100 | 100 |
| $A_{10}$ | 20 | 27 | 27 | 87 | 93 | 100 | 100 | 100 |
| $B_5$ | 0 | 0 | 13 | 93 | 100 | | | |
| $B_{10}$ | 0 | 7 | 27 | 93 | 93 | | | |
| $C_{.25}$ | 0 | 0 | 0 | 0 | 0 | 0 | 0 | 7 |
| $C_1$ | 0 | 0 | 0 | 7 | 7 | 7 | 7 | 13 |
| $C_5$ | 13 | 53 | 80 | 87 | 100 | 100 | 100 | 100 |
| $C_{10}$ | 20 | 40 | 100 | 100 | 100 | 100 | 100 | 100 |
| $D_5$ | 0 | 0 | 0 | 7 | 7 | | | |
| $D_{10}$ | 0 | 7 | 20 | 67 | 80 | | | |
| $E_5$ | 0 | 27 | 87 | 100 | 100 | | | |
| $E_{10}$ | 0 | 47 | 100 | 100 | 100 | | | |
| $F_{10}$ | | | | | | | | |
| $G_{10}$ | 0 | 0 | 40 | 93 | 100 | | | |

TABLE 3-continued

Efficacy Against Unattached *D. polymorpha*

| Chem-ical | Days of Observation | | | | | | | |
|---|---|---|---|---|---|---|---|---|
| | 1 | 2 | 3 | 4 | 5 | 6 | 7 | 8 |
| 3B. Latent Mortality (Percent) After 24 Hours Chemical Exposure | | | | | | | | |
| $C_{10}$ | 0 | 53 | 87 | 93 | 93 | | | |

The subscript denotes concentration in mg/liter.

Efficacy Against Adult *C. fluminea*

Chemical C demonstrated superior efficacy against *C. fluminea*, as shown in Table 4. Chemicals E and F followed with good to excellent efficacy. The overall performance against *C. fluminea* follows the order C>E>F>G>B>D.

TABLE 4

Efficacy Against *C. fluminea*

| Chemical | Days of Observation | | | | | | | |
|---|---|---|---|---|---|---|---|---|
| | 1 | 2 | 3 | 4 | 5 | 6 | 7 | 8 |
| 4A. Cumulative Percent Mortality for Continuous Chemical Exposure | | | | | | | | |
| Controls | 0 | 0 | 0 | 0 | 0 | 0 | 0 | 0 |
| $B_5$ | 0 | 0 | 0 | 0 | 7 | | | |
| $B_{10}$ | 0 | 0 | 0 | 7 | 7 | | | |
| $C_{.25}$ | 0 | 0 | 7 | 7 | 13 | 13 | 13 | 13 |
| $C_1$ | 0 | 0 | 0 | 7 | 53 | 60 | 67 | 67 |
| $C_5$ | 0 | 7 | 47 | 67 | 73 | 73 | 100 | 100 |
| $C_{10}$ | 0 | 7 | 67 | 73 | 80 | 86 | 93 | 100 |
| $D_5$ | 0 | 0 | 0 | 0 | 0 | | | |
| $D_{10}$ | 0 | 0 | 0 | 0 | 7 | | | |
| $E_5$ | 0 | 0 | 0 | 43 | 79 | | | |
| $E_{10}$ | 0 | 0 | 7 | 53 | 80 | | | |
| $F_{10}$ | 0 | 0 | 7 | 33 | 53 | | | |
| $G_{10}$ | 0 | 0 | 0 | 0 | 53 | | | |
| 4B. Latent Mortality (Percent) After 24 Hours Chemical Exposure | | | | | | | | |
| $C_{10}$ | 0 | 0 | 0 | 73 | 80 | | | |

The subscript denotes concentration in mg/liter.

The order of performance follows that seen against *D. polymorpha* but with generally lower efficacies. This difference is explained by the greater ability of *C. fluminea* to avoid noxious chemicals.

Syphon and Feeding Activity

Observation of altered syphoning activity was recorded daily. These observations are useful to determine sublethal responses to various concentrations of chemicals. In general, *D. polymorpha* exhibited less avoidance of chemical exposure than did *C. fluminea* which is useful to understand differences in efficacy. When combined with other stress indicating observations it will be apparent to those skilled in the art that impairing the mollusc's ability to avoid chemical exposure renders it susceptible to synergistic treatments with toxicants such as chlorine.

Inhibition of Attachment

Unattached *D. polymorpha* were placed into chemically treated environments at various concentrations and their natural response to attach to available substratum was observed and recorded. The results are shown in Table 5. These observations are most useful in a preventive control treatment regime. Many of the chemicals exhibited excellent control.

TABLE 5

| Chemical | Days of Observation | | | | | | | |
|---|---|---|---|---|---|---|---|---|
| | 1 | 2 | 3 | 4 | 5 | 6 | 7 | 8 |
| 5A. Percent Inhibition of Attachment for *D. polymorpha* | | | | | | | | |
| Controls | >20 | >20 | >20 | >20 | >20 | >20 | >20 | >20 |
| $A_{.25}$ | 8 | 8 | 8 | 0 | 0 | 0 | 0 | 0 |
| $A_1$ | 27 | 20 | 20 | 20 | 22 | 14 | 7 | 0 |
| $A_5$ | 93 | 87 | 100 | 100 | 100 | | | |
| $A_{10}$ | 100 | 100 | 100 | 100 | 100 | | | |
| $B_5$ | 100 | 100 | 100 | 100 | 100 | | | |
| $B_{10}$ | 100 | 27 | 100 | 100 | 100 | | | |
| $C_{.25}$ | 33 | 40 | 40 | 20 | 20 | 20 | 20 | 13 |
| $C_1$ | 0 | 0 | 0 | 7 | 7 | 7 | 7 | 13 |
| $C_5$ | 87 | 92 | 100 | 100 | 100 | | | |
| $C_{10}$ | 93 | 100 | 100 | | | | | |
| $D_5$ | 93 | 80 | 67 | 60 | 100 | | | |
| $D_{10}$ | 93 | 93 | 100 | 100 | 100 | | | |
| $E_5$ | 100 | 100 | 100 | 100 | 100 | | | |
| $E_{10}$ | 100 | 100 | 100 | 100 | 100 | | | |
| $F_{10}$ | 93 | 100 | 100 | 100 | 100 | | | |
| $G_{10}$ | 100 | 100 | 100 | 100 | 100 | | | |
| 5B. Latent Mortality (Percent) After 24 Hours Chemical Exposure | | | | | | | | |
| $C_{10}$ | 93 | 80 | 100 | 100 | 100 | | | |

The subscript denotes concentration in mg/liter.

Synergy with Oxidizing Biocides

The testing for synergy of the current invention, which employs non-oxidizing chemicals, and conventionally applied oxidizing biocides produced positive results. Further, these results are consistent with the increased susceptibility to noxious chemicals as observed in the stress indications of specimens treated by current invention.

The data for synergy between Chemical A and chlorine is presented in Table 6. The effect is seen as acceleration of time to death and overall higher mortalities. Regimes which repeat this cycle of chemical exposure are expected to produce more ideal results.

TABLE 6

Synergy of Amines and Oxidizing Biocides

| Conditions | Day of Observation | | | | | |
|---|---|---|---|---|---|---|
| | 1 | 2 | 3 | 4 | 5 | 6 |
| Chemical A5 - 24 Hours | 0 | 0 | 20 | 50 | 50 | 50 |
| Chemical A5 - 24 Hours plus 2 Hrs. Chlorine(2) | 0 | 70 | 70 | 70 | 70 | 70 |
| Chemical A5 - 24 Hours plus 2 Hrs. Chlorine(2) | 0 | 40 | 50 | 70 | 70 | 80 |

Notes: The subscript denotes concentration in mg/liter

Summary of Chemical Performance

This invention provides a wide range of chemicals, having various classifications, which work effectively to perform one or more effects which are important to mollusc control. The side-by-side comparison of the tested chemicals and their effect(s) is presented in Table 7. From this presentation, those skilled in the art will be able to select the desired effects from one or a combination of the chemicals tested and to be more effective against each species of mollusc.

TABLE 7

Performance Comparison of All Chemicals

| Chemical | Sub Classification | M1 | M2 | M3 | A |
|---|---|---|---|---|---|
| A | ethoxylated quaternary amine | 4 | 3 | — | 1 |
| B | quaternary amine | 5 | 5 | 5 | 1 |
| C | ethoxylated diamine | 1 | 1 | 1 | 1 |
| D | ethoxylated tertiary amine | 7 | 7 | 6 | 1 |
| E | diamine | 2 | 2 | 2 | 1 |
| F | imidazoline | 3 | 4 | 3 | 1 |
| G | cyclic tertiary imidazoline | 6 | 6 | 4 | 1 |

Notes:
M1 = Mortality against attached *D. polymorpha*
M2 = Mortality against unattached *D. polymorpha*
M3 = Mortality against *C. fluminea*
A = Control of attachment
1 = Highest performance
7 = Lowest Performance It will be apparent to those skilled in the art that there are various applications for the method of the present invention which include, but are not limited to, control and mitigation of macrofouling of molluscs in various aqueous systems such as fresh and saline water supplies used for industrial, steam, electric, municipal and similar applications where macrofouling may cause impairment of system performance. Specific water systems which may be protected according to the method of the present invention include, but are not limited to, once-through and recirculating cooling waters, potable water systems, fire protection systems and other types of auxiliary water systems.

What is claimed:

1. A freshwater molluscicidal method comprising the step of applying to a freshwater target habitat of freshwater molluscs a molluscicidally effective amount of a compound or mixture of compounds selected from the group consisting of ethoxylated and/or propoxylated aliphatic diamines, and salts thereof, wherein said diamines have chain length of 2 to 22 carbon atoms and have at least one mole percent degree of ethoxylation and/or propoxylation.

2. The method according to claim 1 wherein said freshwater molluscs are unattached freshwater molluscs.

3. The method according to claim 1 wherein said freshwater molluscs are attached freshwater molluscs.

4. The method according to claim 1 wherein said molluscs comprise *Dreissena polymorpha*.

5. The method according to claim 1 wherein said molluscs comprise *Corbicula fluminea*.

6. The method according to claim 1 wherein said molluscicidally effective amount is from about 1 to 20 mg/liter in said habitat.

* * * * *